(12) United States Patent
Miller

(10) Patent No.: US 10,471,243 B1
(45) Date of Patent: Nov. 12, 2019

(54) SKINCARE FORMULATION

(71) Applicant: Bruce Wayne Miller, Naples, FL (US)

(72) Inventor: Bruce Wayne Miller, Naples, FL (US)

( * ) Notice: Subject to any disclaimer, the term of this patent is extended or adjusted under 35 U.S.C. 154(b) by 0 days.

(21) Appl. No.: 16/436,282

(22) Filed: Jun. 10, 2019

(51) Int. Cl.

| | |
|---|---|
| *A61K 8/42* | (2006.01) |
| *A61M 35/00* | (2006.01) |
| *A61K 8/36* | (2006.01) |
| *A61K 8/67* | (2006.01) |
| *A61K 8/97* | (2017.01) |
| *A61K 8/9789* | (2017.01) |
| *A61K 8/65* | (2006.01) |
| *A61K 8/49* | (2006.01) |
| *A61L 2/00* | (2006.01) |
| *A61K 8/19* | (2006.01) |

(52) U.S. Cl.
CPC ............ *A61M 35/003* (2013.01); *A61K 8/19* (2013.01); *A61K 8/361* (2013.01); *A61K 8/42* (2013.01); *A61K 8/498* (2013.01); *A61K 8/65* (2013.01); *A61K 8/67* (2013.01); *A61K 8/671* (2013.01); *A61K 8/673* (2013.01); *A61K 8/676* (2013.01); *A61K 8/678* (2013.01); *A61K 8/97* (2013.01); *A61K 8/9789* (2017.08); *A61L 2/0035* (2013.01); *A61K 2800/81* (2013.01); *A61K 2800/87* (2013.01); *A61L 2202/21* (2013.01)

(58) Field of Classification Search
None
See application file for complete search history.

(56) References Cited

U.S. PATENT DOCUMENTS 5,653,970 A * 8/1997 Vermeer ................ A61K 8/602
424/70.1

* cited by examiner

*Primary Examiner* — Nannette Holloman
(74) *Attorney, Agent, or Firm* — Tiffany C. Miller; Inventions International Inc.

(57) ABSTRACT

A moisturizer formulation for topical rejuvenation of the skin containing purified water, sodium tetraborate, lauramide diethanolamine, stearic acid, glycerine, collagen, papaya extract, retinyl palmitate, biotin, grapefruit seed extract, vitamin E acetate, ascorbic acid, linoleic acid, benzyl alcohol, and dehydroacetic acid. The moisturizer formulations of the invention are useful in the rejuvenation of the skin and in particular, after the skin has been exfoliated. The formulation may be retained in an air tight vessel such as an airless pump syringe. About 5 rads to about 10 rads of gamma radiation may be applied to the formulation retained within the air tight vessel.

5 Claims, No Drawings

SKINCARE FORMULATION

BACKGROUND OF THE INVENTION

1. Field of the Invention

This invention relates, generally, to topically applied pharmaceutical formulations to moisturize and rejuvenate the skin after exfoliation. In particular, the invention pertains to the moisturizer formulations containing hydrolyzed collagen and preservatives such as benzylalcohol and dehydroacetic acid.

2. Background Art

The Food and Drug Administration does not regulate many of the chemicals used in the manufacture of cosmetics and skincare products in today's market. This unregulated usage of toxic chemicals such as, parabens, lead, musks, formaldehyde, toluene, hydroquinone, triclosan, and phthalates, within cosmetics and personal skincare products has made unsuspecting consumers susceptible to harmful side effects including, but not limited to, cancer, birth defects, pregnancy complications, contact dermatitis, or hormone interruption. Thus, there is a need for the manufacture of a novel topical moisturizer formulation that contains nontoxic preservatives, nontoxic active ingredients, and nontoxic inactive ingredients, thereby, providing a user with a safe and effective moisturizer for use to rejuvenate a user's skin after a skin exfoliation treatment.

Many moisturizer formulations have toxic parabens configured to bind water to the skin to prevent moisture loss without the use of vitamins. It would be more desirable for a moisturizer formulation to have hydrolyzed collagen and added vitamins to enhance the appearance of dry or damaged skin by reducing flaking, restoring suppleness, to reduce wrinkles and aging signs of the skin.

Many chemicals used in the manufacture of topical moisturizer formulations have been contaminated with harmful microorganisms including, but not limited to, bacteria, mold, yeast, and fungus. For example, microbial contamination and occurrence of skin contamination due to these harmful microorganisms within the chemicals of a formulation may result in bacterial infections of a user including, but not limited to, *Staphylococcus Aureus, Pseudomonas Aeruginosa*, or *Escherichia Coli*. It would be more desirable to remove these contaminants from the novel topical moisturizer formulation during packaging of the product or prior to distribution of the product to the market. Thus, there is a need for microorganism decontamination with gamma irradiation processing using gamma sterilization technology to expose the novel topical moisturizer formulation and its packaging to gamma radiation. As a result, many harmful microorganisms may be reduced or even eliminated from the chemicals used in the novel topical moisturizer formulation.

Many packaging containers used to retain topical moisturizer formulations in today's market are jars having removable lids. The problem with dispensing a topical moisturizer formulation from a jar with a removable lid is that it requires a user to manually dip their finger into the jar to scoop out the product during use, thereby, cross contaminating the product with harmful microorganisms from a user to the product. It would be more desirable to dispense the novel topical moisturizer formulation from an airless pump syringe, thereby eliminating the cross contamination of microorganisms from a user to the product. As a result, the shelf life of the product will be increased and the user will be less susceptible to contracting a disease from microbial contamination during use of the novel topical moisturizer formulation.

However, in view of the prior art considered as a whole at the time the present invention was made, it was not obvious to those of ordinary skill in the pertinent art how the identified needs could be fulfilled.

DESCRIPTION OF THE INVENTION

The long-standing but heretofore unfulfilled need for a moisturizer formulation for topical rejuvenation of the skin containing purified water, sodium tetraborate, lauramide diethanolamine, stearic acid, glycerine, collagen, papaya extract, retinyl palmitate, biotin, grapefruit seed extract, vitamin E acetate, ascorbic acid, linoleic acid, benzyl alcohol, and dehydroacetic acid. The moisturizer formulations of the invention are useful in the rejuvenation of the skin and in particular, after the skin has been exfoliated. The formulation may be retained in an air tight vessel such as an airless pump syringe. About 5 rads to about 10 rads of gamma radiation may be applied to the formulation retained within the air tight vessel. The novel topical moisturizing formulation also includes improvements that overcome the limitations of prior art moisturizer formulations and is now met by a new, useful, and non-obvious invention.

The following description is not to be construed as limiting. Numerous specific details are described to provide a thorough understanding of the invention. However, in certain instances, well know or conventional details are not described in order to avoid obscuring the description. References to one or an embodiment in the present disclosure are not necessarily references to the same embodiment; and, such references refer to at least one.

Reference in this specification to "a general embodiment" or "an alternate embodiment" means that a particular feature, structure, or characteristic described in connection with the embodiment is included in at least one embodiment of the disclosure. The appearances of the phrase "an alternate embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

In a general embodiment, the novel moisturizer formulation has by weight about 58.910% to about 98.190% water, about 0.370% to about 0.630% sodium tetraborate decahydrate, about 3.000% to about 5.000% lauramide diethanolamine, about 11.250% to about 18.750% stearic acid, about 0.040% to about 0.060% retinyl palmitate, about 0.040% to about 0.060% biotin, about 0.040% to about 0.060% ascorbic acid, about 0.040% to about 0.060% cholecalciferol, about 0.040% to about 0.060% vitamin E acetate, about 0.370% to about 0.630% linoleic acid, about 0.070% to about 0.130% plant extract, about 0.070% to about 0.130% hydrolyzed collagen, about 0.370% to about 0.630% citrus seed extract, and about 0.370% to about 0.630% benzylalcohol dehydroacetic acid.

It is within the scope of this invention for the novel moisturizer formulation to include by weight about 78.550% purified water.

In a preferred embodiment, the novel moisturizer formulation has by weight about 0.500% sodium tetraborate decahydrate. Borates such as borax or sodium tetraborate decahydrate are used in the production of skin creams due to their desirable moisture retention properties. Borax also has emulsifying properties that improve the consistency of cosmetic creams and lotions.

In a preferred embodiment, the novel moisturizer formulation has by weight about 4.000% lauramide diethanolamine. Lauramide diethanolamine is a fatty acid derivative of diethanolamine and is capable of increasing foaming capacity and thickening the aqueous water portion of the novel moisturizer formulation.

In a preferred embodiment, the novel moisturizer formulation has by weight about 15.000% stearic acid. Stearic acid is a surfactant capable of lowering the surface tension of oils to allow water to combine with dirt, sweat and excess sebum from the skin and hair to help wash them away.

In a preferred embodiment, the novel moisturizer formulation has by weight about 0.050% retinyl palmitate. Retenoids include, but are not limited to, retinyl palmitate which is also known as vitamin A palmitate. The natural enzymes of a user's skin convert retinyl palmitate to retinol, which is a powerful anti-aging component capable of regenerating the growth of new skin cells to reduce wrinkles. Retinyl Palmitate has benefits when applied to a user's skin including, but not limited to, improving skin tone and thickening the skin to add resiliency and smoothness.

In a preferred embodiment, the novel moisturizer formulation has by weight about 0.050% biotin. Biotin is also known as vitamin B7 and is capable of stimulating the production of new cells and helping oil glands function properly. This results in the healthy appearance of a user's skin when applied topically in the novel moisturizer formulation.

In a preferred embodiment, the novel moisturizer formulation has by weight about 0.050% ascorbic acid. Ascorbic acid is also known as vitamin C. Vitamin C has benefits when applied to a user's skin including, but not limited to, creating a brighter complexion, evening out skin tone, diminishing the appearance of fine lines and wrinkles, shielding skin from the visible impacts of pollution, and improving hydration.

In a preferred embodiment, the novel moisturizer formulation has by weight about 0.050% cholecalciferol. Cholecalciferol is a form of vitamin D and is also known as vitamin D3. Cholecalciferol is an antioxidant, skin conditioner, and moisturizing component of the novel moisturizer formulation.

In a preferred embodiment, the novel moisturizer formulation has by weight about 0.050% vitamin E acetate. It is within the scope of this invention for vitamin E acetate to include, but not be limited to alpha-tocopheryl acetate (ATA), tocopherol acetate, or vitamin E acetate 50%. Alpha-tocopheryl acetate is a specific form of vitamin E that's often found in skin care products and dietary supplements. Vitamin E is known for its antioxidant and anti-inflammatory properties.

In a preferred embodiment, the novel moisturizer formulation has by weight about 0.500% linoleic acid. Linoleic acid is an Omega-6 essential fatty acid and is also referred to as vitamin F. Linoleic acid has skincare benefits including, but not limited to, strengthening the skin's protective barrier and providing moisture to a user's skin without weighing down the skin.

In a preferred embodiment, the novel moisturizer formulation has by weight about 0.100% plant extract. It is within the scope of this invention for the plant extract to include, but not be limited to, papaya extract. In a preferred embodiment, the plant extract has been manipulated by at least one process to produce a preservative free and most optimal biocompatibility with the skin of a user. At least one process the plant extract may undergo includes, but is not limited to, zeodration drying process, titration using high performance liquid chromatography, and the addition of glycerin.

In a preferred embodiment, the novel moisturizer formulation has by weight about 0.100% hydrolyzed collagen. Hydrolyzed Collagen is a hydrolysate of animal or fish collagen derived by acid, enzyme, or other method of hydrolysis. In a preferred embodiment the hydrolyzed collagen is derived from including, but not limited to, a fish source. Hydrolyzed collagen in the novel moisturizer formulation is capable of enhancing the appearance of dry or damaged skin by reducing flaking and restoring suppleness.

In a preferred embodiment, the novel moisturizer formulation has by weight about 0.500% citrus seed extract. It is within the scope of this invention for the citrus seed extract to be grapefruit seed extract. Grapefruit seed extract is a nontoxic preservative in the novel topical moisturizer formulation. In a preferred embodiment, the novel moisturizer formulation has by weight about 0.500% grapefruit seed extract.

In a preferred embodiment, the novel moisturizer formulation has by weight about 0.500% benzylalcohol dehydroacetic acid (DHA). It is within the scope of the current invention for the novel topical moisturizer formulation to have at least two preservatives. At least two preservatives of the novel topical moisturizer formulation are grapefruit seed extract and benzylalcohol DHA. Benzylalcohol DHA comprises benzylalcohol and dehydroacetic acid to inhibit growth of microbes including, but not limited to, bacteria, mold, yeast, and fungus within the novel topical moisturizer formulation.

In an alternate embodiment, the novel topical moisturizer formulation may be exposed to about 5 rads to about 10 rads of gamma radiation. It is within the scope of this invention for the gamma radiation process to occur either before, during, or after packaging of the product within an air tight vessel in an attempt to reduce or eliminate microorganisms from the novel topical moisturizer formulation.

The novel topical moisturizer formulation is retained in an air tight vessel including, but not limited to, a bottle, a jar, a bag, a syringe, or an airless pump syringe. It is within the scope of this invention for the air tight vessel to be any sterile dispenser capable of retaining the novel topical moisturizer formulation. A preferred embodiment of the sterile dispenser is an airless pump bottle or an airless pump syringe capable of protecting the novel topical moisturizer formulation by preventing excessive exposure to air and preventing exposure to a user's cross contamination, thus increasing product shelf life and protecting the formulation from harmful microorganisms associated with cross contamination by a user. The airless bottle or the airless syringe has no dip tube but rather a diaphragm that rises to evacuate the product, thus, a user does not come into contact with the entire reservoir retaining the novel topical moisturizer formulation. When user depresses the pump, it creates a vacuum effect, drawing the product upwards. A user can use almost all of the products without any waste left over and the problem of standard pumps not working appropriately is eliminated.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

The invention claimed is:

1. A formulation, comprising, by weight:
   about 58.910% to about 78.55% water;
   about 0.370% to about 0.630% sodium tetraborate decahydrate;
   about 3.000% to about 5.000% lauramide diethanolamine;
   about 11.250% to about 18.750% stearic acid;
   about 0.040% to about 0.060% retinyl palmitate;
   about 0.040% to about 0.060% biotin;
   about 0.040% to about 0.060% ascorbic acid;
   about 0.040% to about 0.060% cholecalciferol;
   about 0.040% to about 0.060% vitamin E acetate;
   about 0.370% to about 0.630% linoleic acid;
   about 0.070% to about 0.130% plant extract;
   about 0.070% to about 0.130% hydrolyzed collagen;
   about 0.370% to about 0.630% citrus seed extract; and,
   about 0.370% to about 0.630% benzylalcohol dehydroacetic acid.

2. A method for reducing or eliminating microorganisms from the formulation according to claim 1, comprising applying about 5 rads to about 10 rads of gamma radiation to the formulation of claim 1.

3. The formulation of claim 1, wherein the formulation is retained in an air tight vessel.

4. The formulation of claim 3, wherein said air tight vessel having an airless pump mechanism.

5. A method for reducing or eliminating microorganisms from the formulation according to claim 3, comprising applying about 5 rads to about 10 rads of gamma radiation to the formulation of claim 3.

* * * * *